(12) United States Patent
Ferrandon et al.

(10) Patent No.: US 11,628,424 B2
(45) Date of Patent: Apr. 18, 2023

(54) MULTIMETALLIC CATALYSTS FOR METHANATION OF CARBON DIOXIDE AND DRY REFORMING OF METHANE

(71) Applicant: UCHICAGO ARGONNE, LLC, Chicago, IL (US)

(72) Inventors: Magali Ferrandon, Steger, IL (US); Gokhan Celik, Clarendon Hills, IL (US); Massimiliano Delferro, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 43 days.

(21) Appl. No.: 16/984,836

(22) Filed: Aug. 4, 2020

(65) Prior Publication Data
US 2022/0040677 A1  Feb. 10, 2022

(51) Int. Cl.
| | | |
|---|---|---|
| B01J 23/75 | (2006.01) | |
| B01J 23/755 | (2006.01) | |
| B01J 21/10 | (2006.01) | |
| B01J 23/10 | (2006.01) | |
| B01J 23/22 | (2006.01) | |
| B01J 23/745 | (2006.01) | |
| B01J 37/02 | (2006.01) | |
| B01J 37/18 | (2006.01) | |
| B01J 37/08 | (2006.01) | |
| C07C 1/04 | (2006.01) | |
| B01J 21/04 | (2006.01) | |

(52) U.S. Cl.
CPC ............. *B01J 23/755* (2013.01); *B01J 21/04* (2013.01); *B01J 21/10* (2013.01); *B01J 23/10* (2013.01); *B01J 23/22* (2013.01); *B01J 23/745* (2013.01); *B01J 37/0203* (2013.01); *B01J 37/0207* (2013.01); *B01J 37/086* (2013.01); *B01J 37/18* (2013.01); *C07C 1/044* (2013.01); *C07C 2521/04* (2013.01); *C07C 2521/10* (2013.01); *C07C 2523/10* (2013.01); *C07C 2523/755* (2013.01)

(58) Field of Classification Search
CPC ... B01J 21/04; B01J 21/10; B01J 23/22; B01J 23/745; B01J 23/755; B01J 37/0203; B01J 37/0207; B01J 37/086; B01J 37/18; C07C 1/044; C07C 2521/04; C07C 2521/10; C07C 2523/10; C07C 2523/755
See application file for complete search history.

(56) References Cited

U.S. PATENT DOCUMENTS 4,937,218 A * 6/1990 Ramirez de Aqudelo ................. C10G 47/02 502/238
2010/0197482 A1 * 8/2010 Basset .................. B01J 37/0209 502/154

OTHER PUBLICATIONS

Coperet, C. et al., 2016, Chemical Reviews, 116(2), 323-421.*
Nichio, N.N. et al., 2000, Catalysis Today, 62, 231-240.*
Zienkiewicz-Machnik, M. et al, 2018, Catalysis Today, 308, 38-44.*
(Continued)

*Primary Examiner* — Brian A McCaig
(74) *Attorney, Agent, or Firm* — Foley & Lardner LLP

(57) ABSTRACT

Processes for forming multimetallic catalysts by grafting nickel precursors to metal oxide supports. Dry reforming reaction catalysts having nickel and promotors grafted to metal oxides supports. Methanation reaction catalysts having nickel and promotors grafted to metal oxides supports.

17 Claims, 8 Drawing Sheets

E = Al, Ce, Mg, Si, Ti
M = B, Cu, Co, Fe, Mn, Sn, Mg, V, Zn

(56) References Cited

OTHER PUBLICATIONS

Barroso-Quiroga, et al., "Catalytic activity and effect of modifiers on Ni-based catalysts for the dry reforming of methane," International Journal of Hydrogen Energy 35(11), pp. 6052-6056 (2010).

Chai, et al., "A Nickel-Based Perovskite Catalyst with a Bimodal Size Distribution of Nickel Particles for Dry Reforming of Methane," ChemCatChem 10(9), pp. 2078-2086 (2018).

Chen, et al., "High carbon-resistance Ni/CeAlO3—Al2O3 catalyst for CH4/CO2 reforming," Applied Catalysis B: Environmental 136-137, pp. 260-268 (2013).

Das, et al., "Silica-Ceria sandwiched Ni core-shell catalyst for low temperature dry reforming of biogas: Coke resistance and mechanistic insights," Applied Catalysis B: Environmental 230, pp. 220-236 (2018).

Djinovic, et al., "Influence of active metal loading and oxygen mobility on coke-free dry reforming of Ni—Co bimetallic catalysts," Applied Catalysis B: Environmental 125, pp. 259-270 (2012).

Garcia-Dieguez, et al., "Nanostructured Pt- and Ni-based catalysts for CO2-reforming of methane," Journal of Catalysis 270(1), pp. 136-145 (2010).

Gotz, et al., "Renewable Power-to-Gas: A technological and economic review," Renewable Energy 85, pp. 1371-1390 (2016).

Han, et al., "Uncoupling the size and support effects of Ni catalysts for dry reforming of methane," Applied Catalysis B: Environmental 203, pp. 625-632 (2017).

Kambolis, et al., "Ni/CeO2—ZrO2 catalysts for the dry reforming of methane," Applied Catalysis A: General 377(1-2), pp. 16-26 (2010).

Li, et al., "Dry reforming of methane over Ni/La2O3 nanorod catalysts with stabilized Ni nanoparticles," Applied Catalysis B: Environmental 202, pp. 683-694 (2017).

Li, et al., "Yolk-Satellite-Shell Structured Ni-Yolk@Ni@SiO2 Nanocomposite: Superb Catalyst toward Methane CO2 Reforming Reaction," ACS Catalysis 4(5), pp. 1526-1536 (2014).

Lofberg, et al., "Ni/CeO2 based catalysts as oxygen vectors for the chemical looping dry reforming of methane for syngas production," Applied Catalysis B: Environmental 212, pp. 159-174 (2017).

Shiratori, et al., "Internal reforming SOFC running on biogas," International Journal of Hydrogen Energy 35(15), pp. 7905-7912 (2010).

Sutthiumporn & Kawi, "Promotional effect of alkaline earth over Ni—La2O3 catalyst for CO2 reforming of CH4: Role of surface oxygen species on H2 production and carbon suppression," International Journal of Hydrogen Energy 36(22), pp. 14435-14446 (2011).

Theofanidis, et al., "Enhanced Carbon-Resistant Dry Reforming Fe—Ni Catalyst: Role of Fe," ACS Catalysis 5(5), pp. 3028-3039 (2015).

Tu, et al., "Dry reforming of methane over a Ni/Al2O3 catalyst in a coaxial dielectric barrier discharge reactor," Journal of Physics D: Applied Physics 44(27), 274007, 10 pages (2011).

Wang, et al., "CO2 reforming with methane over small-sized Ni@SiO2 catalysts with unique features of sintering-free and low carbon," Applied Catalysis B: Environmental 235, pp. 26-35 (2018).

Wang, et al., "Synthesis, characterization and catalytic performances of Ce-SBA-15 supported nickel catalysts for methane dry reforming to hydrogen and syngas," International Journal of Hydrogen Energy 37(1), pp. 19-30 (2012).

Wolfbeisser, et al., "Methane dry reforming over ceria-zirconia supported Ni catalysts," Catalysis Today 277(2), pp. 234-245 (2016).

Zhang, et al., "Ceria-Doped Ni/SBA-16 Catalysts for Dry Reforming of Methane," ACS Catalysis 3(8), pp. 1855-1864 (2013).

Zhang, et al., "Nickel nanoparticles embedded in mesopores of AlSBA-15 with a perfect peasecod-like structure: A catalyst with superior sintering resistance and hydrothermal stability for methane dry reforming," Applied Catalysis B: Environmental 224, pp. 488-499 (2018).

Zuo, et al., "Dry Reforming of Methane on Single-Site Ni/MgO Catalysts: Importance of Site Confinement," ACS Catalysis 8(10), pp. 9821-9835 (2018).

* cited by examiner

MULTIMETALLIC CATALYSTS FOR METHANATION OF CARBON DIOXIDE AND DRY REFORMING OF METHANE

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to catalysts, more specifically to catalysts for dry reforming of methane and methanation of carbon dioxide.

BACKGROUND

There is a great interest in the efficient transformation of greenhouse gases for chemicals and fuels. For example, carbon dioxide ($CO_2$) and carbon monoxide (CO) can both be hydrogenated to methane.

Hydrogenation of $CO_2$ to methane, also known as $CO_2$ methanation or the Sabatier process, is an attractive catalytic reaction owing to its potential to mitigate problems caused by the global $CO_2$ emission and practical advantages of producing synthetic natural gas to store renewable energy and in-situ utilization of $CO_2$-rich space atmosphere into vital consumables for space missions. The process may occur by:

$$CO_2 + 4H_2 \rightarrow CH_4 + 2H_2O (\Delta_r H_{298} = -165 kJ/mol)$$

$CO_2$ methanation has been reported to be catalyzed by precious metals supported on inorganic oxides. However, nickel-based heterogeneous catalysts are preferred because of their low cost and high abundance. It has also been reported that catalytic performance of $CO_2$ methanation highly depends on catalyst attributes, particularly the dispersion of the metal sites. Heterogeneous catalysts synthesized by conventional synthesis techniques, such as impregnation and precipitation, lead to the formation of large nanoparticles with low dispersion. Under reaction conditions, large nanoparticles promote irreversible changes, such as sintering of the metal sites and coke formation, that lower the catalytic performance and deactivate the catalysts.

In addition to the formation of useful materials such as methane, processes can be used to transform greenhouse cases into useful fuels. For example, dry reforming of methane ("DRM") can comprehensively utilize $CH_4$ and $CO_2$ to produce syngas (CO, $H_2$) which is desirable for methanol synthesis or Fisher-Tropsch process. As one example:

$$CH_4 + CO_2 \rightarrow 2H_2 + 2CO (\Delta_r H_{298} = 247.3 kJ/mol)$$

Nickel-based catalysts are the most studied catalysts for this reaction. DRM is not regarded as an industrially mature process because of the poor durability of the catalysts, coke formation, and sintering of the active sites. A large amount of steam needs to be co-fed in order to eliminate carbon formations. There is good potential for successful application of full-scale reforming plants where only small amounts of steam would be needed. A key feature in a dry-reforming catalyst is its dispersion, which provides additional active sites but also resistance to sintering. Both supports and promoters could possibly enhance the activity and stabilize the active sites. In order to achieve high dispersion, the method of preparation (i.e., how the nickel (and/or promoter) is deposited onto the supports) has significant effect. Most catalysts are prepared using the incipient wetness technique, which leads to 3D clusters and poor dispersion, favoring sintering and coke formation. For example, coking can occur as follows:

Boudouard reaction: $2CO \rightarrow C + CO_2$

Methane decomposition: $CH_4 \rightarrow C + 4H$

Catalytic systems for both dry reforming and methanation suffer from drawbacks, including a tendency to coke heavily and have sintering occur at the catalytic sites. Prior research has considered a number of options for addressing these drawbacks. In particular, prior work has considered novel reactor technologies, modification of the supports in the catalytic system, the use of multimetallic catalysts, and the variation of particle size for the catalysts. However, there remains a need for a catalyst system that provides for reduced coking and resistance to sintering of the catalytic sites.

SUMMARY

Embodiments described herein relate generally to a method of forming a multimetallic catalyst. The method comprises grafting an organometallic promotor comprising a metal selected from the group consisting of B, Cu, Co, Fe, Mn, Sn, Mg, V, and Zn and an organic ligand, onto a metal oxide support selected from the group consisting of $Al_2O_3$, $CeO_2$, MgO, $SiO_2$, $TiO_2$, forming a promotor-support material, calcining the organometallic promotor in air to form a calcined promotor-support material; grafting an organonickel precursor grafted onto the calcined promotor-support material; and reducing the organonickel grafted promotor-support material to form an active multimetallic catalyst.

Other embodiments generally relate to a methanation reaction catalyst. The catalyst comprises a metal oxide support selected from the group consisting of $Al_2O_3$, $CeO_2$, MgO, $SiO_2$, $TiO_2$. A promotor is grafted to the metal oxide support, the promotor comprising a metal selected from the group consisting of B, Cu, Co, Fe, Mn, Sn, Mg, V, and Zn. Nickel is grafted to the metal oxide support and comprising 10-90% surface coverage of the metal oxide support.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

(FIG. 4A), 700° C. (FIG. 4B), 750° C. (FIG. 4C), and 800° C. (FIG. 4D) at $CH_4:CO_2=1:1$.

Figure 1:
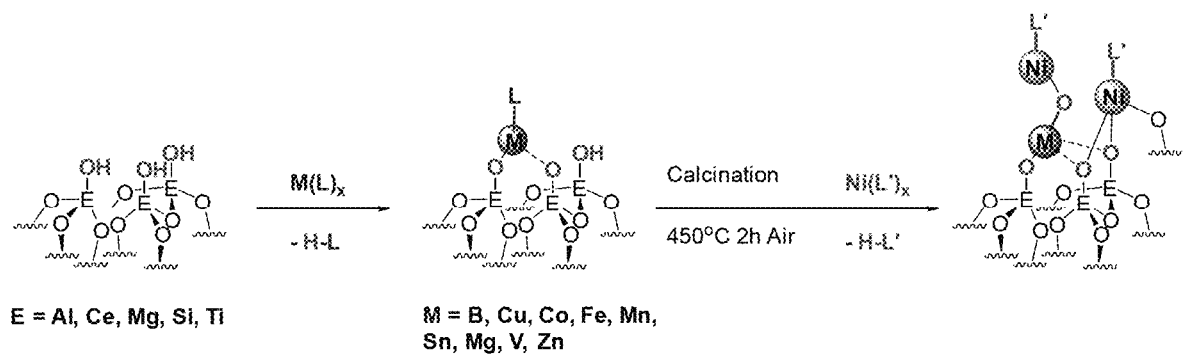
FIG. 1 illustrates the general synthesis of Ni/M'/$E_yO_x$ catalysts by grafting technique.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to catalyst materials. Specifically, one embodiment provides a synthetic approach to bimetallic catalysts supported on metal oxides with improved activity, thermal stability, and resistance to coking under dry reforming of methane (1) or methanation (2) reactions:

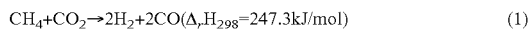

$$CH_4 + CO_2 \rightarrow 2H_2 + 2CO \quad (\Delta_r H_{298} = 247.3 \text{kJ/mol}) \quad (1)$$

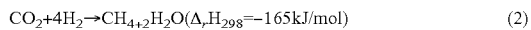

$$CO_2 + 4H_2 \rightarrow CH_4 + 2H_2O \quad (\Delta_r H_{298} = -165 \text{kJ/mol}) \quad (2)$$

Coking: Boudouard reaction: $2\ CO \rightarrow C + CO_2$

Methane decomposition: $CH_4 \rightarrow C + 4\ H$

In one embodiment, a process for forming catalysts utilizes a sequential grafting synthetic technique that allows for better isolation and dispersion of Ni sites to prevent the catalysts from deactivation, by either formation of coke or agglomeration of active sites (sintering). Grafting of organometallic precursors in liquid phase on reactive inorganic oxide surfaces creates well-defined, highly-dispersed sites for $CO_2$ methanation or dry reforming reaction. In one embodiment, the grafting technique uses surface organometallic chemistry ("SOMC") metalation. The SOMC technique uses hydroxyl groups from the oxide supports to anchor each metal precursor. After heat treatment, upon removal of the ligand, the metal gets anchored and well dispersed with strong interactions with the oxide support or (promoter oxide). During reaction at high temperature, metal tends to agglomerate to form large particles, therefore one embodiment starts with very well dispersed reactants to make it more difficult for them to agglomerate. Grafting results in surface cover of 10-90%, such as 50% as targeted in the experimental examples below.

In one embodiment, organometallic precursors that react with hydroxyl groups from the surface of the support oxides at room temperature can be used. In an alternative embodiment, the metalation can be done at higher temperature for less reactive organometallic precursors. In one embodiment using the SOMC methanation grafting technique, there is a need to pre-reduce the catalysts to activate the active species, such as metallic Ni.

FIG. 1 illustrates one embodiment of the synthesis of (bi)metallic catalysts $Ni/M'/E_yO_x$ by grafting technique. An organometallic precursor $(M(L)_x)$ where M is Boron (B), Copper (Cu), Cobalt (Co), Iron (Fe), Manganese (Mn), Tin (Sn), Magnesium (Mg), Vanadium (V), or Zinc (Zn) and L is a ligand, is grafted first onto an oxide support ($E_yO_x$=aluminum oxide ($Al_2O_3$), cerium oxide ($CeO_2$), magnesium oxide (MgO), silicon dioxide ($SiO_2$), titanium dioxide ($TiO_2$)), then calcined in air (e.g., 400-600° C., such as at 450° C.) to form the metal oxides. Then an organonickel precursor M'L'(FIG. 2) is grafted onto $M'/E_yO_x$, which then may be further processed, such as by in-situ pre-reduction, to form the active phase in the catalyst. In one embodiment, in-situ pre-reduction includes exposure of 10% hydrogen inert gas at 800° C. for 2 hours. L are ligands that are present in the organometallic precursors M' and L' is ligand from the organonickel precursor. The inorganic metal oxide supports may be selected from $Al_2O_3$, $CeO_2$, MgO, $SiO_2$, $TiO_2$. Broadly, the catalyst is a $Ni/M'/E_yO_x$ catalysts and $Ni/E_yO_x$, for unpromoted catalysts.

Figure 2:
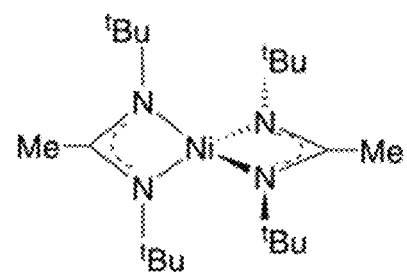
FIG. 2 is one embodiment of the nickel (Ni) precursor, Bis(N,N'-di-t-butylacetamidinato)nickel(II), used for synthesis.
Figure 3:
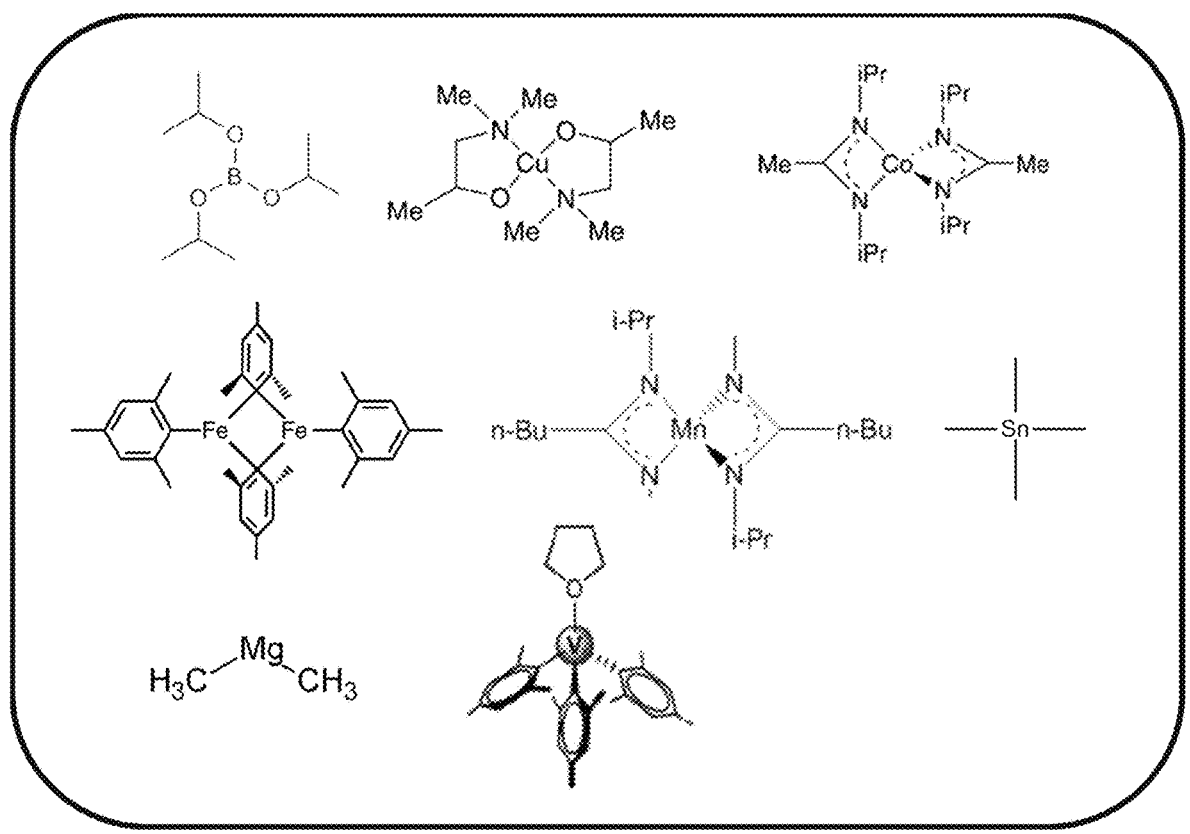
FIG. 3 illustrates various exemplary embodiments of organometallic precursors for promoters in accordance with the embodiments described herein.

FIG. 2 is one embodiment of the nickel precursor,Bis(N,N'-di-t-butylacetamidinato)nickel(II) used for experimental synthesis examples. FIG. 3 illustrates embodiments of organometallic precursors used for the anchoring of the promoters onto the oxide supports in experimental synthesis examples.

Experimental Procedures.

Deposition of the Promoters onto the Supports by SOMC.

For each support, 50% coverage of a monolayer by a promoter was chosen as a target. For each combination, 600 mg support was weighed in an 8 mL glass vial pre-loaded with a magnetic stir bar. Under stirring, the solid supports were then pre-wetted with dry toluene to ensure homogeneous deposition of organometallic precursors. Various stock solutions of organometallic precursors (B, Cu, Co, Fe, Mn, Sn, Mg, V, Zn) (see FIG. 3) in toluene were then dispensed into each vial. After dispensing the stock solution, additional toluene was dispensed to adjust the total liquid volume to 4 mL. The vials were then placed onto a shaker and let it for 24 hours at 600 rpm. The well plates were then centrifuged for 10 minutes, and then the supernatant was removed and 2 mL fresh toluene was added. The procedure was repeated 5 times. After removal of the last supernatant, the vials were then removed from the glovebox and placed onto another shaker in a fume hood without the cap to let them dry under air environment over 2 days yielding organometallic-support material (i.e., promotors grafted onto the metal oxide support forming a promotor-support material). The samples were then calcined in air at 450° C. for 2 hours. For promoter-less sample testing, the supports were also calcined to ensure proper comparison with Ni/M/support.

Deposition of the Nickel onto the Supports by SOMC.

For each promoted support, a loading of 50% coverage nickel was targeted; in one embodiment, 50% of the hydroxyl groups (as the anchoring group on the support surface) are half filled, i.e. 50% of the hydroxyl groups will have one bond with one Nickel so it is atomically dispersed. A organometallic nickel precursor such as bis(N,N'-di-t-butylacetamidinato)nickel(II) is utilized. Other precursors maybe used, so long as they are reactive enough with the hydroxyl groups at the relevant temperatures, such as low temperature (room temperature to 50° C.). The organometallic precursor is grafted onto the metal oxide supports or onto the promotor-modified metal oxide supports by SOMC. The dried solids were then brought back into the glovebox for the addition of nickel precursor (see FIG. 2). The same procedure was repeated as above, without the calcination, forming multimetallic material.

In one embodiment, multimetallic material was either pre-reduced in-situ with 5 to 20% $H_2$ at 700-850° C. (e.g., 800° C.) for 1-3 hours (e.g., for 2 hours) before dry reforming or with 5-20% $H_2$ in an inert environment (e.g., Ni or Ar) at 200-600° C. (e.g., 500° C.) for 1-3 hours (e.g., 2 hours) before methanation. Roughly 60 catalysts were crafted as experimental samples using this general technique.

Carbon Dioxide Methanation Examples

In one embodiment, the catalysts are methanation catalysts. In embodiments for methanation, the catalyst synthesis comprises of a method for grafting an organonickel precursor onto inorganic metal oxide supports ($SiO_2$, $Al2O_3$, $CeO_2$, $TiO_2$, and MgO) to produce novel catalysts. In a further embodiment, an initial grafting of organometallic promoters (B, Cu, Co, Fe, Mn, Sn, Mg, V, and Zn) onto the inorganic metal oxide supports ($SiO_2$, $Al_2O_3$, $CeO_2$, $TiO_2$, and MgO) is followed by grafting the organonickel precursor to produce novel catalysts. After reduction, such as at 550° C. in hydrogen, the catalysts exhibited high activity and stability for $CO_2$ methanation.

Experimental samples for forty catalysts were tested. After pre-activation (500° C. in $H_2$), some of the catalysts exhibited high activity and stability for 25 hours. The conditions for testing were: total flowrates for each reactor of either 6 mL/min or 9 mL/min were used, of which 3 mL/min $H_2$, 1 mL/min He, and varying flowrates of 30% $CO_2$/Ar and $N_2$ to keep the total flowrate the same. This gives a $H_2$:$CO_2$=5.4, 4, 3 and 2. Catalysts were pre-reduced with 10% $H_2$/Ar for 2 hours at 500° C. The temperatures tested were 150-300° C. (5° C./min) with an increment of 50° C., followed by a stability testing at 500° C. for 15 hours.

Figure 7:
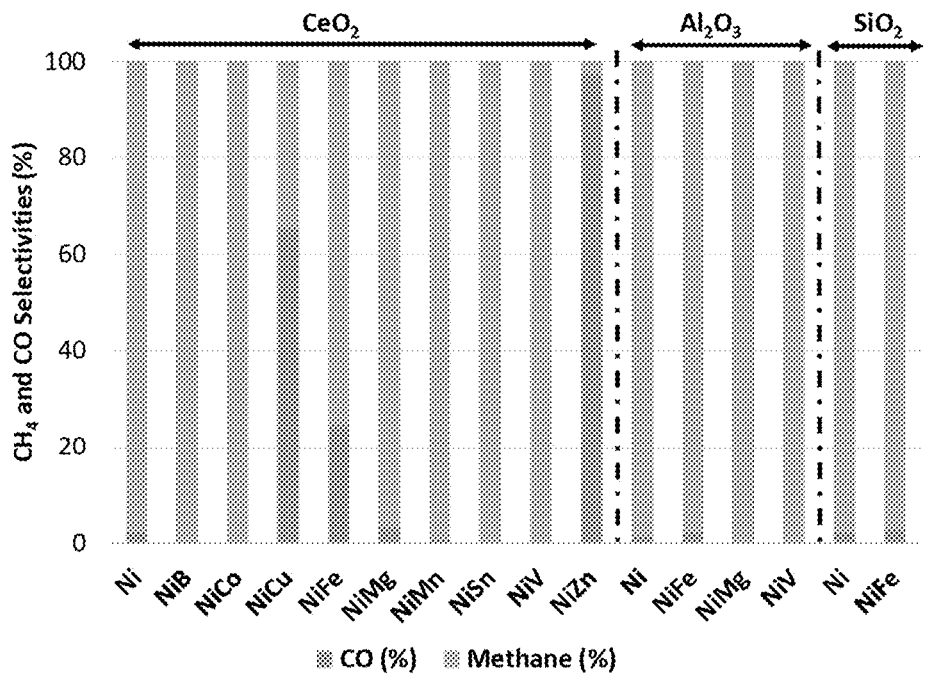
FIG. 7 illustrates the selectivities to carbon monoxide and methane for the noted catalysts for the methanation reaction.
Figure 8:
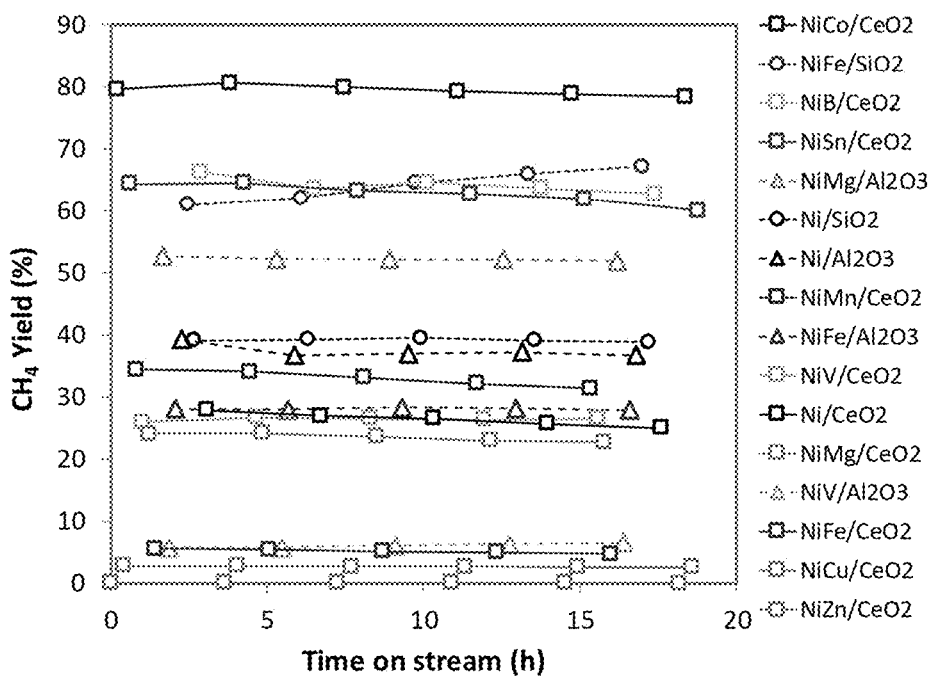
FIG. 8 shows the methane yield as a function of the time on stream for the catalysts for the methanation reaction.

FIG. 7 illustrates the selectivities to carbon monoxide and methane for the noted catalysts. FIG. 8 shows the methane yield as a function of the time on stream for the catalyst. Selectivities to methane were improved for B-, Co-, Mn-, Sn-, and V-doped Ni/$CeO_2$ compared to Ni/$CeO_2$ alone; while on alumina, Mg and V were enhanced (FIG. 7). Stability testing at 300° C. was performed over 15 hours to see whether the catalysts suffer from deactivation (FIG. 8). Most of the catalysts show a stable methane yield over the period tested with the exception of NiB/$CeO_2$ and NiSn/$CeO_2$ and to some extent NiCo/$CeO_2$ that deactivated. On the other hand, methane yield increased steadily using NiFe/$SiO_2$.

Dry Reforming of Methane Examples

Catalytic conversion of $CO_2$ into useful chemicals continue to attract researchers' attention due to its potential to mitigate the problems caused by global $CO_2$ emission. Dry reforming of methane converts two greenhouse gases ($CO_2$ and $CH_4$) into syngas (CO and $H_2$), which can be subsequently transformed into value-added chemicals and fuels by methanol to olefins or Fischer-Tropsch ("FT") processes. Currently, extensive coking necessitates co-feeding large amount of steam which constitutes a major operational cost and hampers the feasibility and widespread utilization of dry reforming technology.

One embodiment comprises a method of producing catalysts by a grafting technique based on surface organometallic chemistry that is based on anchoring the organometallic sites onto reactive inorganic metal oxide surfaces. This leads to more defined and higher dispersed metal oxide species. Embodiments described herein employ this technique to graft promoters (B, Cu, Co, Fe, Mn, Sn, Mg, V, and Zn) as organometallic precursors (FIG. 3) and organonickel (FIG. 2) as main active species, onto metal oxide supports ($SiO_2$, $AlO_3$, $CeO_2$, and MgO) for highly active and stable catalysts for DRM.

Figure 4A:
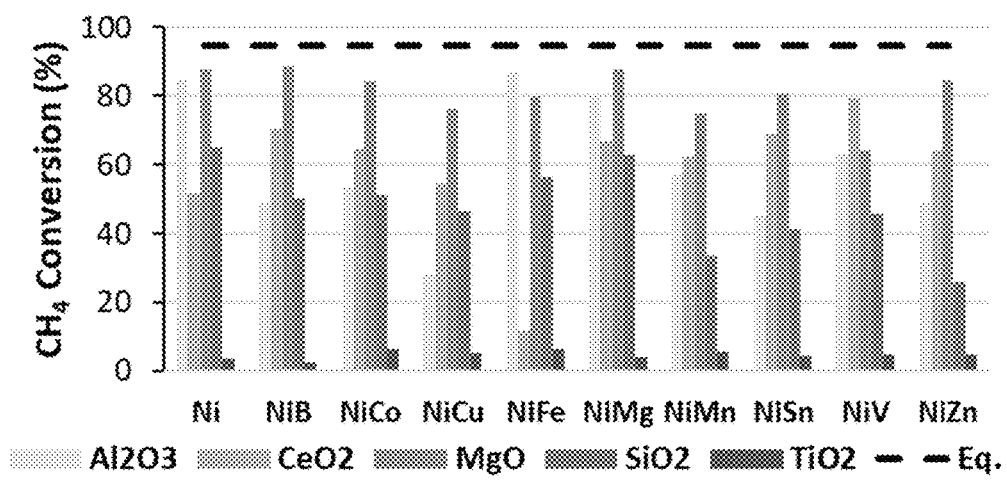
FIGS. 4A-4D show methane conversion at 650° C.
Figure 4B:
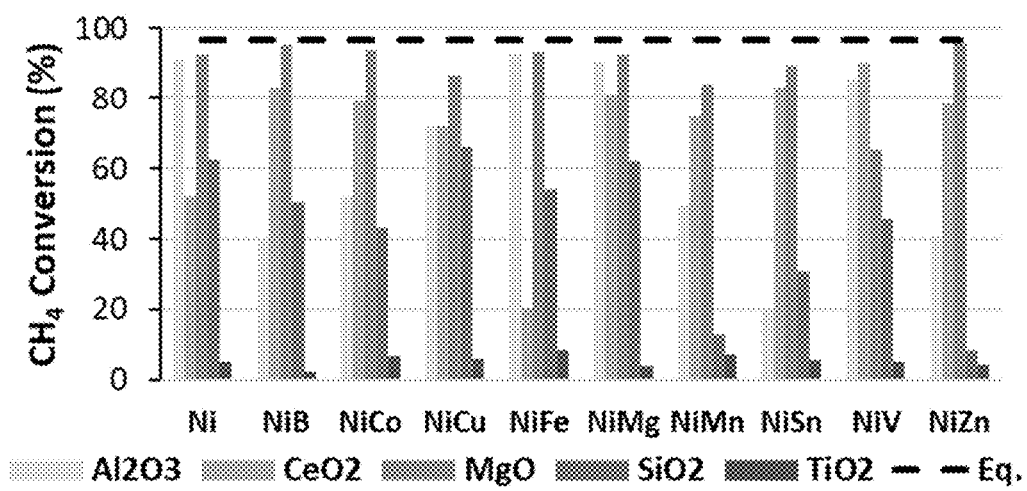
Figure 4C:
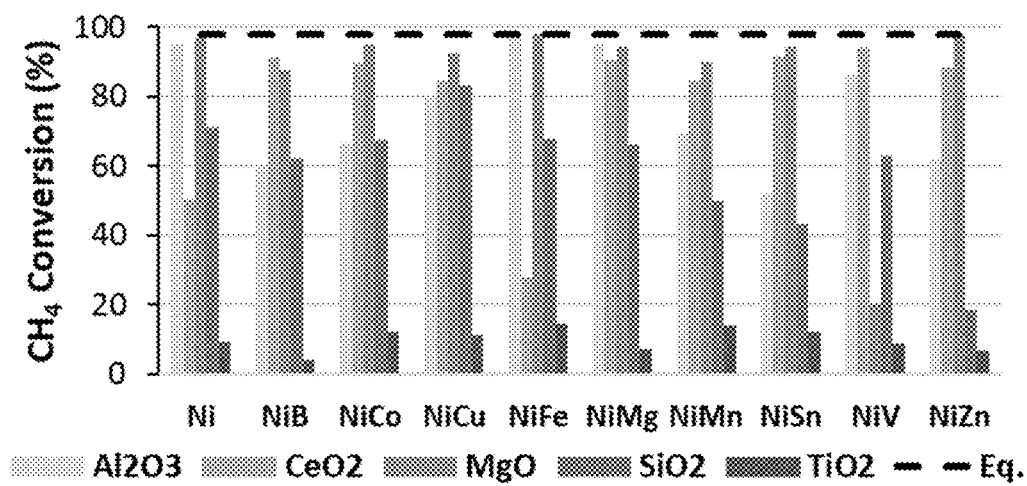
Figure 4D:
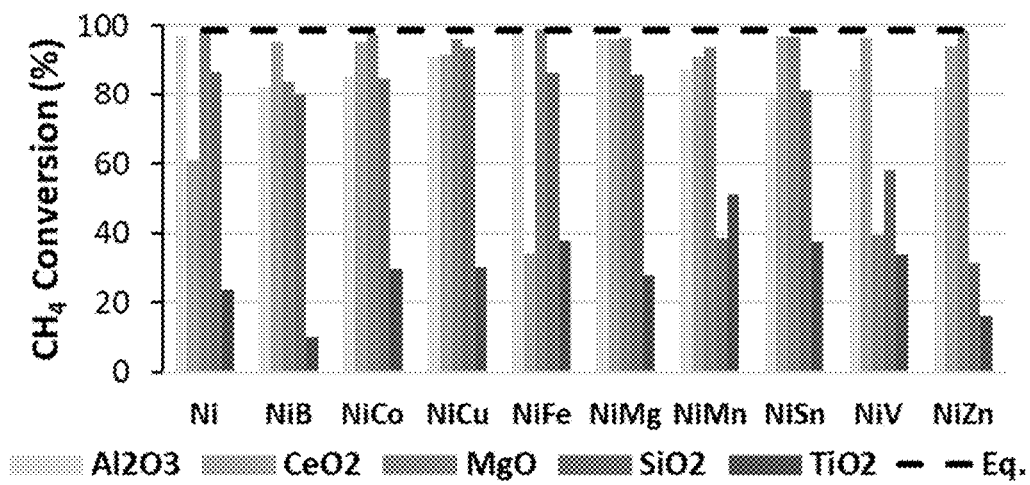
Figure 4E:
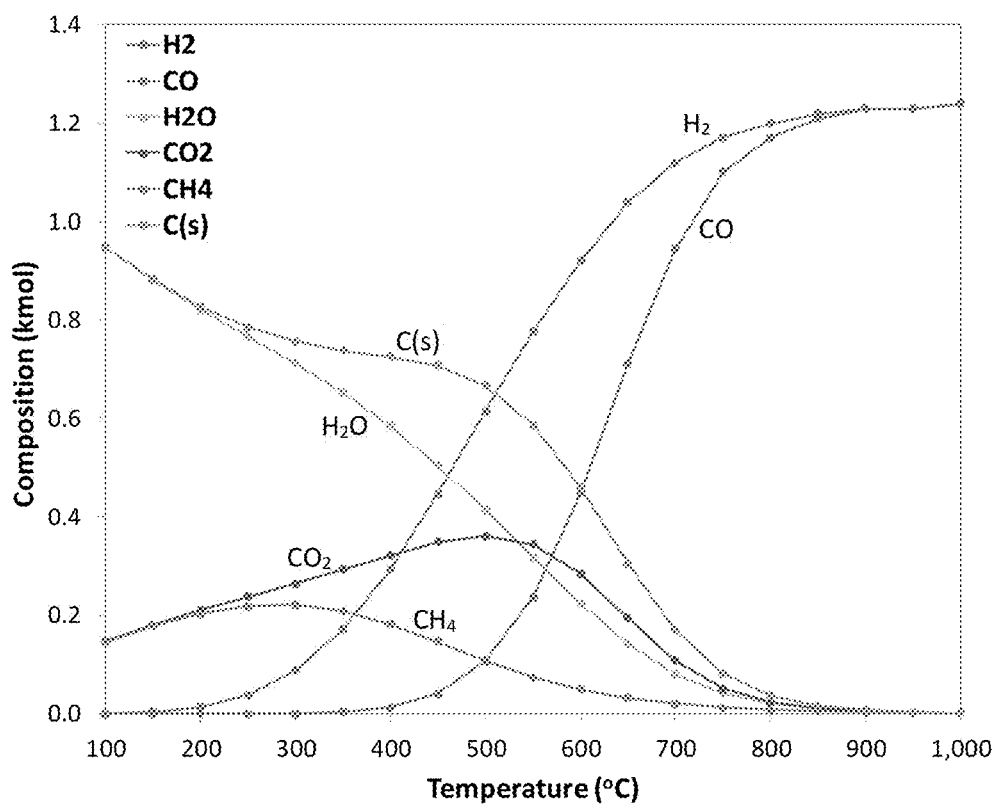
FIG. 4E shows the equilibrium data (calculated by HSC) for the dry reforming reaction using our experimental conditions.
Figures 5A, 5B:
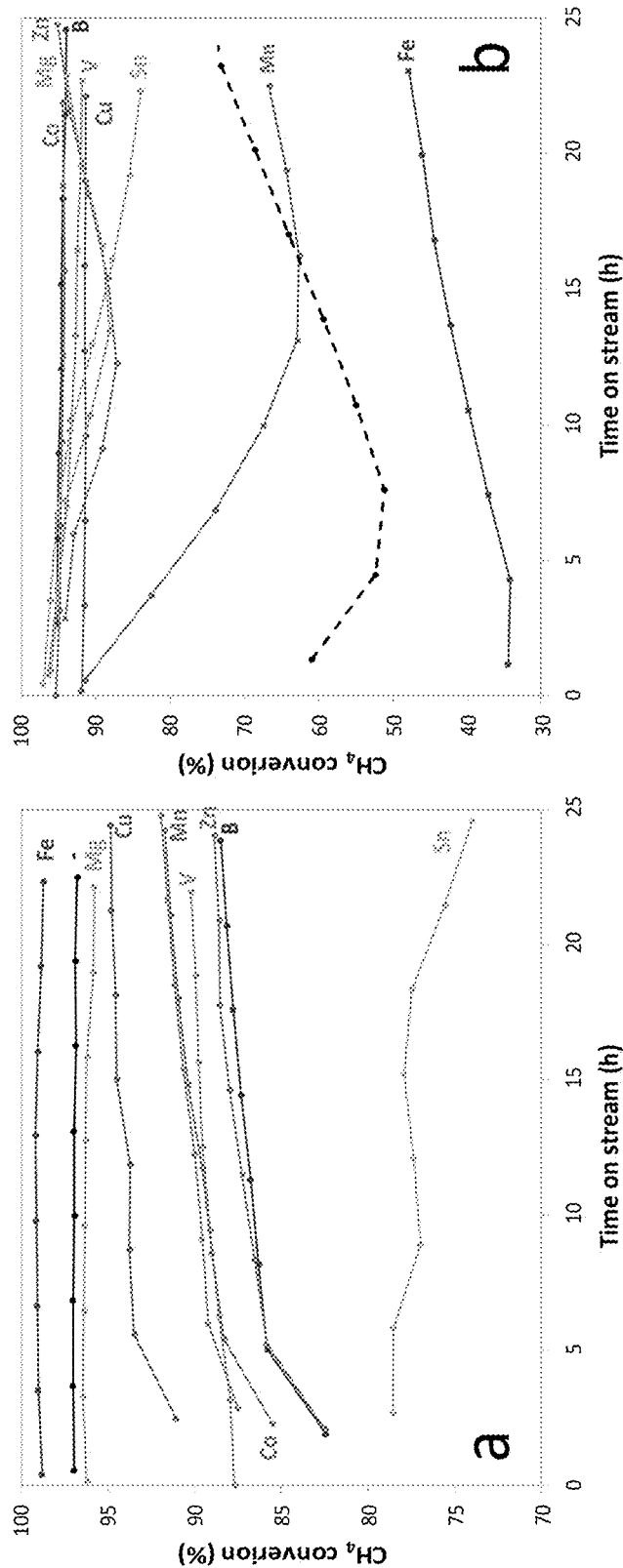
FIGS. 5A-5E show stability data at 800° C. for Ni/support (–) and Ni/promoter/support catalysts based on various supports: $Al_2O_3$(FIG. 5A), $CeO_2$ (FIG. 5B), MgO (FIG. 5C), $SiO_2$ (FIG. 5D), and $TiO_2$ (FIG. 5E) for the dry reforming reaction.
Figures 5C, 5D:
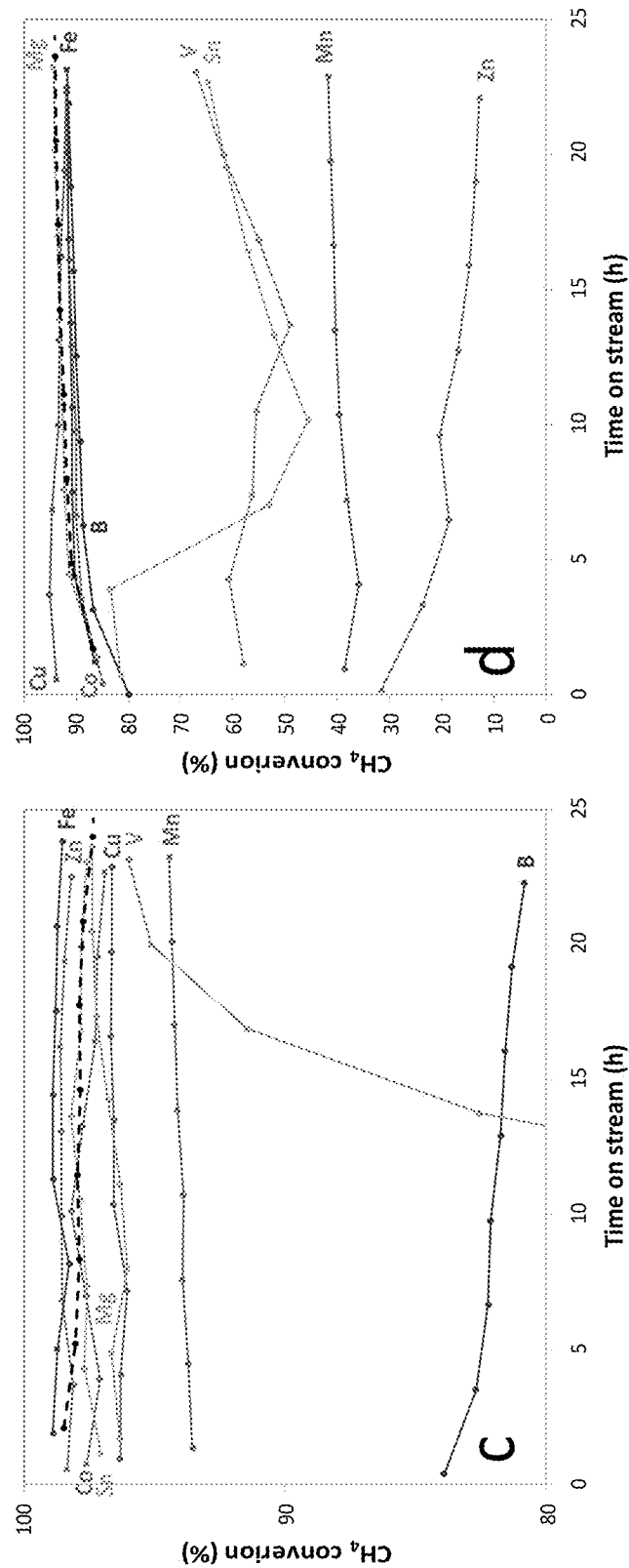
Figure 5E:
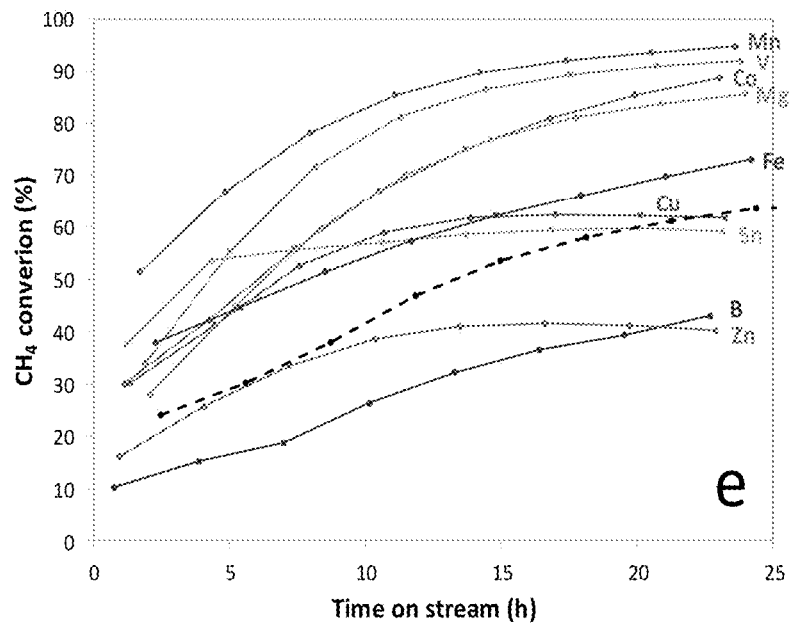
Figure 6:
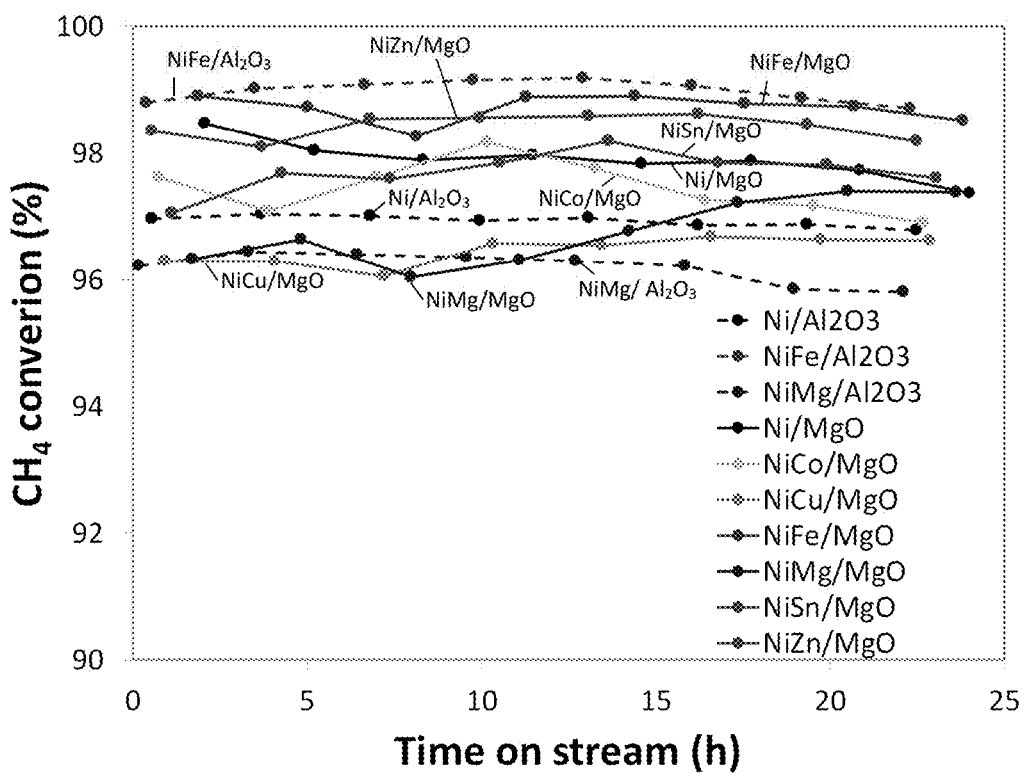
FIG. 6 shows the methane conversion results for the ten best performing experimental sample catalysts for the dry reforming reaction.

FIGS. 4A-4D show methane conversion at 650° C. (FIG. 4A), 700° C. (FIG. 4B), 750° C. (FIG. 4C), and 800° C. (FIG. 4D) at $CH_4$:$CO_2$=1:1. Conditions: Total flowrates for each reactor of 7 mL/min were used; of which 6 mL/min 10% $CO_2$, 10% $CH_4$/Ar, and 1 mL/min He ($CH_4$:$CO_2$=1:1). Catalysts were pre-reduced with 10% $H_2$/Ar for 2 hours at 800° C. The temperatures tested were 650-800° C. (5° C./min) with an increment of 50° C., followed by a stability testing at 800° C. for 24 hours. FIG. 4E shows the equilibrium data (calculated by HSC) for the dry reforming reaction using our experimental conditions. FIGS. 5A-5E show further results of experimental catalysts. The twenty-six combinations show over 90% methane conversion for 25 hours and 10 combinations show over 95% methane conversion at 800° C. The catalysts developed using this strategy remain active (25 hours). FIG. 6 shows the conversion results for the ten best performing experimental sample catalysts.

The 10 most performant catalysts for the dry reforming were characterized by scanning electron microscope ("SEM"), transmission electron microscopy ("TEM") (imaging), powder diffraction (crystallinity) and temperature-programmed reduction (metal-support interaction) and Raman (coke formation) techniques. A correlation between the dispersion of nickel and the activity was found: the higher the dispersion of nickel, the more active the Ni/M'/$E_yO_x$ catalyst compared to unpromoted Ni (Ni/$E_yO_x$) catalyst. In addition, the Ni/promoter/support forms less coke formation compared to Ni/support. In particular, Ni/Fe/$Al_2O_3$ and Ni/Fe/MgO were more active than Ni/$Al_2O_3$ and Ni/MgO, respectively, and were stable over a period of 25 hours.

Definitions

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially" and "about" used throughout this Specification are used to describe and account for small fluctuations. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method of forming a multimetallic catalyst comprising:
    grafting an organometallic promotor comprising a metal selected from the group consisting of B, Cu, Co, Fe, Mn, Sn, Mg, V, and Zn and an organic ligand, onto a metal oxide support selected from the group consisting of $Al_2O_3$, $CeO_2$, MgO, $SiO_2$, and $TiO_2$, forming a promotor-support material;
    calcine the organometallic promotor in air to form a calcined promotor-support material;
    grafting an organonickel precursor grafted onto the calcined promotor-support material; and
    reducing the organonickel grafted promotor-support material to form an active multimetallic catalyst.

2. The method of claim 1, wherein reducing comprises reduction with 5-20% hydrogen at 200-600° C. for 2 hours and the active multimetallic catalyst is a methanation reaction catalyst.

3. The method of claim 2, wherein reducing comprises reduction with 10% hydrogen at 500° C. for 2 hours.

4. The method of claim 2, wherein the metal oxide support comprises $CeO_2$.

5. The method of claim 4, wherein the metal is selected from the group consisting of B, Co, Mn, Sn, and V.

6. The method of claim 4, wherein the metal is selected from the group consisting of Mg and V.

7. The method of claim 4, wherein the metal is Fe.

8. The method of claim 1, wherein the wherein the oxide support comprises $Al_2O_3$.

9. The method of claim 1, wherein reducing comprises reduction with 5-20% hydrogen at 700-850° C. for 2 hours and the active multimetallic catalyst is a dry reforming reaction catalyst.

10. The method of claim 9, wherein oxide support is selected from the group consisting of $Al_2O_3$ and MgO.

11. The method of claim 1, wherein reducing comprises reduction with 10% hydrogen at 800° C. for 2 hrs.

12. A methanation reaction catalyst comprising:
a metal oxide support selected from the group consisting of $Al_2O_3$, $CeO_2$, MgO, $SiO_2$, $TiO_2$;
a promotor grafted to the metal oxide support, the promotor comprising a metal selected from the group consisting of Mg and V; and
organonickel grafted to the metal oxide support and comprising 10-90% surface coverage of the metal oxide support.

13. The methanation reaction catalyst of claim 12, wherein the metal oxide support comprises $CeO_2$.

14. The methanation reaction catalyst of claim 12, wherein the oxide support comprises $Al_2O_3$.

15. A methanation reaction catalyst comprising:
a metal oxide support selected from the group consisting of $CeO_2$;
a promotor grafted to the metal oxide support, the promotor comprising a metal selected from the group consisting of B, Cu, Co, Fe, Mn, Sn, Mg, V, and Zn; and
organonickel grafted to the metal oxide support and comprising 10-90% surface coverage of the metal oxide support.

16. The methanation reaction catalyst of claim 15, wherein the metal is selected from the group consisting of B, Co, Mn, Sn, and V.

17. The methanation reaction catalyst of claim 15, wherein the metal is selected from the group consisting of Mg and V.

* * * * *